(12) United States Patent
Waggoner et al.

(10) Patent No.: US 7,534,477 B1
(45) Date of Patent: May 19, 2009

(54) WRISTBAND FORM WITH OVERLAMINATE LABEL

(75) Inventors: Bryce C. Waggoner, Monroe, OH (US); Patrick A. Konkol, Troy, OH (US); Sherry L. Bannister, Kettering, OH (US); Erin Staub, Tipp City, OH (US); Kevin R. Keys, Danville, VA (US); David F. Laurash, Bellbrook, OH (US)

(73) Assignee: The Standard Register Company, Dayton, OH (US)

( * ) Notice: Subject to any disclaimer, the term of this patent is extended or adjusted under 35 U.S.C. 154(b) by 351 days.

(21) Appl. No.: 10/685,095

(22) Filed: Oct. 10, 2003

(51) Int. Cl.
*B32B 9/00* (2006.01)
*B32B 33/00* (2006.01)
*A61B 5/117* (2006.01)
*G09C 3/00* (2006.01)

(52) U.S. Cl. .................. 428/40.1; 428/41.8; 428/42.2; 428/42.3; 428/43; 40/633; 283/74; 283/75; 283/81

(58) Field of Classification Search ............... 428/40.1, 428/42.3, 41.8, 42.2, 43; 40/633, 665; 283/74, 283/75, 81, 900
See application file for complete search history.

(56) References Cited

U.S. PATENT DOCUMENTS

| RE30,786 E | * | 11/1981 | Wiebe | 40/665 |
|---|---|---|---|---|
| 4,906,025 A | | 3/1990 | Schreindl | 281/45 |
| 5,026,084 A | | 6/1991 | Pasfield | 283/75 |
| 5,045,426 A | | 9/1991 | Maierson et al. | 430/126 |
| 5,653,472 A | | 8/1997 | Huddleston et al. | 283/75 |
| 5,785,354 A | * | 7/1998 | Haas | 283/74 |
| 5,846,624 A | | 12/1998 | Denklau et al. | 428/42.3 |
| 5,914,197 A | | 6/1999 | Goudjil | 428/437.5 |
| 5,933,993 A | | 8/1999 | Riley | 40/633 |
| 6,000,160 A | | 12/1999 | Riley | 40/633 |
| 6,016,618 A | | 1/2000 | Attia et al. | 40/633 |
| 6,067,739 A | | 5/2000 | Riley | 40/633 |
| 6,438,881 B1 | | 8/2002 | Riley | 40/633 |

OTHER PUBLICATIONS

About PDC; http//www.pdcorp.com/company/about-pdc.html; 2 pages.

(Continued)

*Primary Examiner*—Patricia L Nordmeyer
(74) *Attorney, Agent, or Firm*—Dinsmore & Shohl LLP

(57) ABSTRACT

A patient wristband form has a transparent ply with an upper surface and a lower surface, and a pressure sensitive adhesive coating on the lower surface. A release ply has an upper surface and a lower surface, with a release coating on the upper surface. The transparent ply is removably mounted on the upper surface of the release ply by the pressure sensitive adhesive coating. A die cut in the transparent ply defines an elongated wristband. An opaque coating is provided on the upper surface of the transparent ply in a central portion of the elongated wristband. A die cut in the transparent ply defines an overlaminate label that is sized to cover at least a part of the central portion of the elongated wristband, thereby covering indicia printed on the opaque coating. A paper ply may also be mounted on the release ply by pressure sensitive adhesive. The paper ply defines a plurality of labels that may be printed at the same time as the wristband.

22 Claims, 2 Drawing Sheets

OTHER PUBLICATIONS

Protective Pocket Wristbands; http://www.pdcorp.com/healthcare/pocket_wristbands.html; 2 pages.
Thermal & Laser Lables; http://www.pdcorp.com/healthcare/datamate_labels.html; 2 pages.
Write-On Wristbands; http://www.pdcorp.com/healthcare/write_on_bands.html; 4 pages.
Insert Wristbands & Cards; http://www.pdcorp.com/healthcare/insert_wristbands.html; 6 pages.

* cited by examiner

WRISTBAND FORM WITH OVERLAMINATE LABEL

CROSS-REFERENCE TO RELATED APPLICATIONS

None.

STATEMENT REGARDING FEDERALLY SPONSORED RESEARCH OR DEVELOPMENT

Not Applicable.

BACKGROUND OF THE INVENTION

The present invention relates to a printable wristband form. More particularly, the present invention relates to a form having a wristband with an opaque portion, or a portion that is not substantially transparent, accompanied by a transparent label for affixation to the wristband after printing to protect printed information.

It is a common practice in hospitals to identify patients with a bracelet or band containing the patient's name or other identification information. The band is generally secured around the wrist of a patient so that hospital personnel can properly identify the patient during his stay. However, while this has been an effective method of identifying patients, many hospitals have had problems correlating patient information on specimens, drug prescriptions, physician's orders, and the like. Clerical errors in handling such routine matters can result in the wrong medicine being dispensed, or the wrong treatment being given to a patient.

Several attempts have been made to improve the correlation of patient information to various hospital forms. For example, Falla, U.S. Pat. No. 4,122,947 teaches a pre-packaged patient identification kit which includes a wristband, a specimen container, and a label for attachment to a patient's record, all of which have been provided with identical patient information. Weichselbaum et el, U.S. Pat. No. 3,848,112, teaches a patient identification system in which an identification bracelet secured to a patient is used to dispense a series of tags which are magnetically coded with patient information. This method requires the use of a tag reader as well as decoding circuitry. These methods are complex and difficult to implement.

U.S. Pat. No. 5,653,472, issued Aug. 5, 1997, to Huddleston et al, discloses a form having detachable labels and a wristband. The form includes a face ply adhered to a liner ply by a pressure sensitive adhesive. The face ply includes a first portion and a second portion, where the first portion is die cut to form a wristband and the second portion is die cut to form a series of detachable labels. The form may be printed in a single pass through a printer to provide the wristband and labels with correlating printed indicia. The form of the '472 patent thus is a substantial improvement over prior wristband arrangements. However, the indicia on the wristband taught in the '472 patent are subject to being removed or rendered illegible as a result of exposure to various liquids, and as a result of wear from the surface of the wristband rubbing against various surfaces.

Accordingly, there is still a need in the art for an identification system which includes a wristband as well as an accompanying series of labels or tags which can be efficiently provided with correlating identification information, and which also includes a transparent protective label for application to the wristband surface after it is printed with appropriate indicia.

SUMMARY OF THE INVENTION

The present invention meets this need by providing a single form which includes a wristband, as well as an accompanying series of detachable labels and a transparent label for application to the wristband over indicia printed on the wristband. The patient wristband form includes a transparent ply having an upper surface and a lower surface, and a pressure sensitive adhesive coating on the lower surface of the transparent ply. A release ply has an upper surface and a lower surface, and a release coating on the upper surface of the release ply. The transparent ply is removably mounted on the upper surface of the release ply by the pressure sensitive adhesive coating. A die cut in the transparent ply defines an elongated wristband. An opaque coating is provided on the upper surface of the transparent ply in a central portion of the elongated wristband. A die cut in the transparent ply defines an overlaminate label. The overlaminate label is sized to cover at least a part of the central portion of the elongated wristband so as to cover indicia printed on the opaque coating.

The release ply is substantially larger than the transparent ply, and further comprises a paper ply having an upper surface and a lower surface. The lower surface of the paper ply has a pressure sensitive adhesive coating. The paper ply is mounted on the release ply by the pressure sensitive adhesive. One or more labels may be defined by die cuts in the paper ply. The transparent ply may define a plurality of colored labels that can be affixed to the elongated wristband. The pressure sensitive adhesive coating on the lower surface of the transparent ply may be pattern coated such that an area beneath the elongated wristband central portion is free of adhesive. The transparent ply may be die cut to define one or more additional labels.

The transparent ply and the paper ply may be directly adjacent each other so as to provide a patient wristband form of substantially uniform thickness, whereby the form may advantageously be printed by means of a laser printer or an ink jet printer. The release ply may define a perforation line extending there across, between the transparent ply and the paper ply. The transparent ply may further define one or more circular die cut holes in the elongated wristband adjacent each end thereof, whereby the elongated wristband may be secured in place around the wrist of a patient by a clasp which engages one hole at each end of the wristband. The opaque coating on the upper surface of the transparent ply in a central portion of the elongated wristband may comprise a coating of a white, opaque ink. The transparent ply may comprise a ply of film material, such as for example a ply of substantially clear polyester film material.

The top ply may have a portion which is substantially transparent and another portion which is not substantially transparent. A die cut in the top ply defines an elongated wristband, including at least part of the portion of the top ply which is not substantially transparent. This defines a print indicia receiving area. A die cut in the transparent portion of the top ply defines an overlaminate label. The overlaminate label is sized to cover at least a part of the print indicia receiving area.

Accordingly, it is an object of the present invention to provide a patient wristband form which can be printed with a non-impact printer and in which the printed indicia on the wristband are protected by means of an integral overlaminate label. Other objectives of the present invention will be apparent in light of the description of the invention embodied herein.

DETAILED DESCRIPTION OF THE PREFERRED EMBODIMENT

Figure 1:
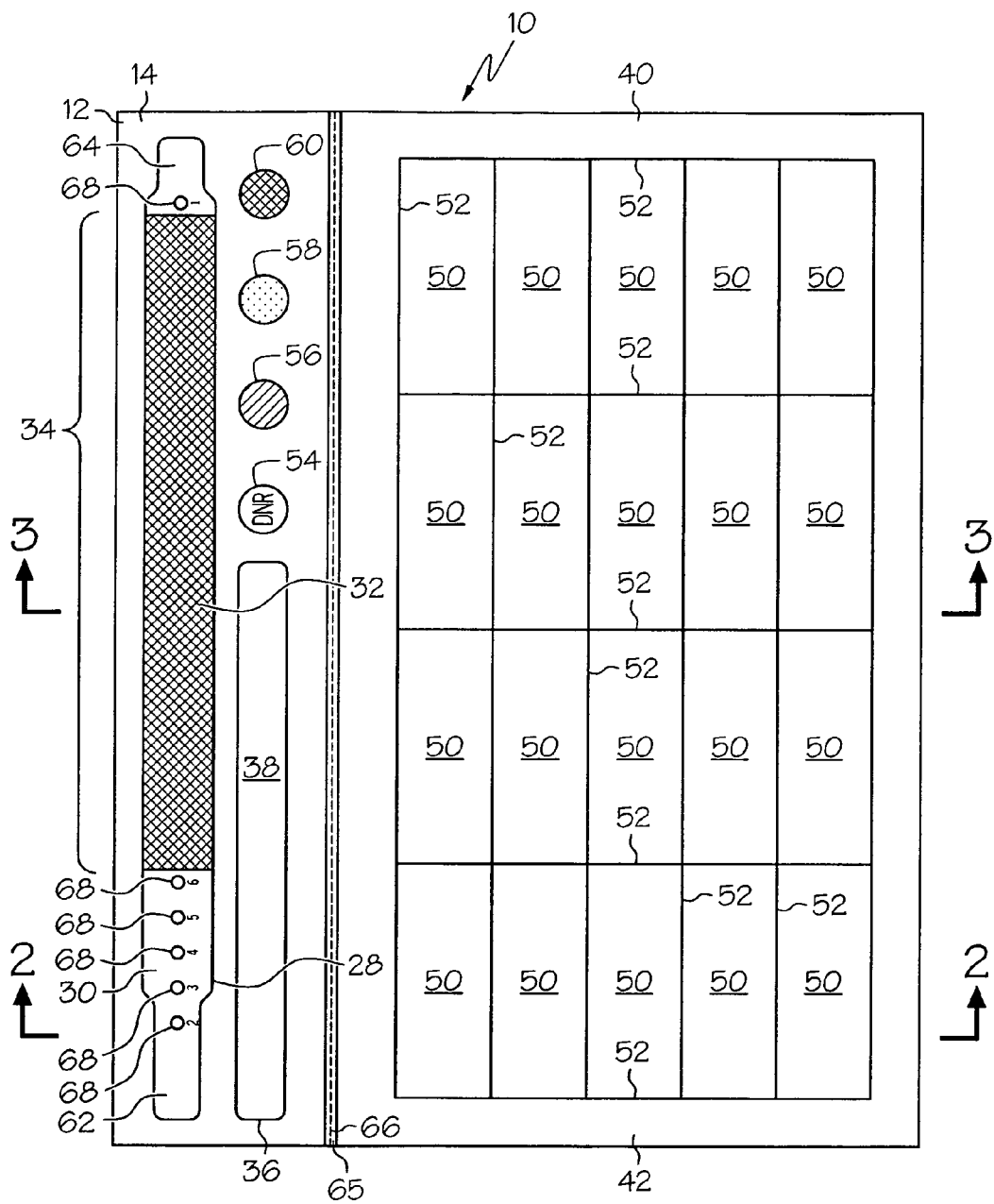
FIG. 1 is a plan view of a patient wristband form according to the present invention.
Figure 2:
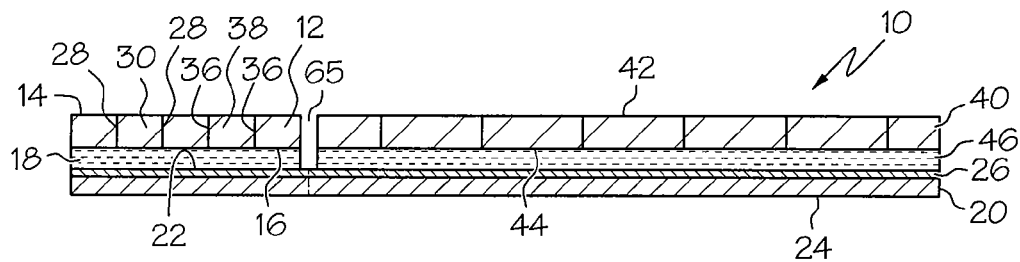
FIG. 2 is a cross sectional view of the patient wristband form of the present invention, taken generally along line 2-2 in FIG. 1.
Figure 3:
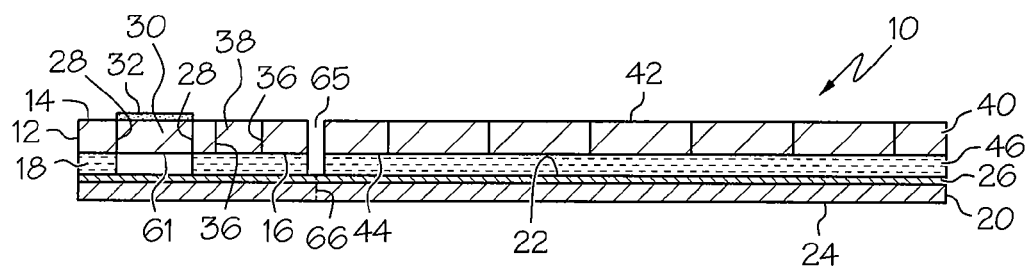
FIG. 3 is a cross-sectional view of the patient wristband form of the present invention, taken generally along line 3-3 in FIG. 1.

Reference is made to FIGS. 1-3 which illustrate a patient wristband form 10 constructed according to the present invention. It should be noted that, for clarity and ease of understanding in the cross-sectional views of FIGS. 2 and 3, the thickness of each of the layers and plies is significantly exaggerated in relation to the other dimensions of the drawings. The form 10 includes a transparent ply 12 having an upper surface 14 and a lower surface 16. The transparent ply 12 may comprise a ply of film material, more preferably a ply of substantially clear polyester film material. A pressure sensitive adhesive coating 18 is provided on the lower surface of the transparent ply 12. A release ply 20 has an upper surface 22, and a lower surface 24, with a release coating 26 on the upper surface 22 of the release ply 20. The transparent ply 12 is removably mounted on the upper surface 22 of the release ply 20 by the pressure sensitive adhesive coating 18. The transparent ply 12 includes a die cut 28 defining an elongated wristband 30.

An opaque coating 32 is provided on the upper surface of the transparent ply in a central portion 34 of the elongated wristband 30. It is preferable that the coating comprises a layer of white, substantially opaque ink, as this provides excellent contrast with human and machine readable indicia that may be printed on this part of the wristband 30. A die cut 36 in the transparent ply 12 defines an overlaminate label 38. The overlaminate label 38 is sized to cover at least a part of the central portion 34 of the elongated wristband 30. More particularly, the overlaminate label 38 is intended to be used to cover those human readable and machine readable indicia that are printed on the opaque coating 32. As explained more fully below, these indicia may be printed by means of a non-impact printer, such as for example a laser printer, a thermal or thermal transfer printer, or an ink jet printer. As such, however, the printed indicia may not be as durable as desired. The use of the overlaminate label 38 protects the printed information and maintains its legibility.

It will be noted that the release ply 20 is substantially larger than the transparent ply 12, and that the wristband form further comprises a paper ply 40 having an upper surface 42 and a lower surface 44. The lower surface 44 of the paper ply has a pressure sensitive adhesive coating 46. The paper ply 40 is mounted on the release ply 20 by the pressure sensitive adhesive 46. One or more labels 50 are defined by die cuts 52 in the paper ply 40. Adhesives 46 and 18 may differ from each other, or may be the same pressure sensitive adhesive, depending in part upon the specific use to which the form is put. Labels 50 may be applied to various surfaces requiring more or less aggressive adhesive characteristics, and the adhesive 46 for labels 50 may be selected on this basis.

The transparent ply 12 may define one or more additional colored labels 54, 56, 58, and 60 that can be affixed to the elongated wristband 30. Labels 54-60 may provide a highly visible indication of specific information relating to the patient wearing the wristband. Some of the colored labels, such as label 54, may have preprinted indicia, whereas others of the printed labels, such as labels 56-60, may only be printed with solid ink colors. The labels 54-60 are defined by appropriate circular die cuts, but may, if desired, be fashioned as rectangular or square labels. The labels 54-60 need not be opaque so long as they are appropriately colored to convey the desired information about the wearer of a wristband. It will be appreciated that one or more of the labels 54-60 may be overprinted with additional indicia at the time that the balance of the form 10 is printed, as discussed more fully below.

It is preferred that the pressure sensitive adhesive coating 18 on the lower surface 16 of the transparent ply 12 be pattern-coated such that area 61 beneath the elongated wristband central portion 34 is free of adhesive. It is even more preferred that the adhesive 18 be limited to the end tabs 62 and 64 at opposite ends of the wristband 30. It will be appreciated that, as a result, adhesive material will not adhere directly to the patient's skin when the wristband 30 is wrapped around the patient's wrist.

It will be noted that the transparent ply 12 and the paper ply 40 are directly adjacent each other so as to provide a patient wristband form 10 of substantially uniform thickness. That is, the space 65 between ply 12 and ply 40 is relatively small such that the form 10 approximates a sheet of uniform thickness which feeds through laser printers, thermal printers, and ink jet printers without difficulty and with little likelihood of jamming. A perforation line 66 extends across the release ply 20 between the transparent ply 12 and the paper ply 40. As will be explained more fully below, the perforation line permits the form 10 to be separated into two pieces after printing to facilitate the application of the wristband to the wrist of a patient and to facilitate the use of the labels 50 in designating various forms and other items as associated with the patient.

Figure 4:
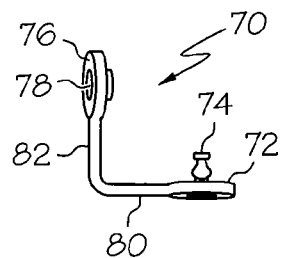
FIG. 4 is an enlarged perspective view of a clip of the type that may be used to secure the wristband around the wrist of a patient.

The transparent ply 12 further defines one or more circular die cut holes 68 in the elongated wristband 30, adjacent each end thereof. The elongated wristband 30 may be secured in place around the wrist of a patient by a clasp 70, shown in FIG. 4. Clasp 70 engages one hole 68 at each end of the wristband 30, to hold the ends together in conjunction with adhesive 18 on the lower surface 16 of the wristband 30 adjacent the end tabs 62 and 64. Clasp 70 is typically molded from a relatively pliable plastic material. The clasp 70 has a post portion 72 defining a post 74, and a opening portion 76 defining an opening 78. Legs 80 and 82 are relatively thin and flexible, and permit the post portion 72 and the opening portion 76 to be brought together with post 74 extending through holes 68 at opposite ends of the wristband 30 and with post 74 being snapped into opening 78. This results in the opposite ends of the wristband 30 being securely engaged by the clasp 70 and the wristband 30 secured to the wrist of a patient.

Other constructions are contemplated within the scope of the present invention. For example, rather than utilize a clear, transparent film for the ply 12 with a coating of white, opaque ink in the central portion 34, the ply 12 may consist of a top ply 12 having at least a portion which is substantially transparent and a portion which is not substantially transparent. This may for example include a ply which consists of two separate and discrete portions, one of which consists of an opaque film or other material, and the other of which consists of a transparent material, such as a transparent film. These two portions may be adhesively joined, for example, or simply mounted on the release ply 20 directly abutting. For example, a white polyester film portion and a clear polyester film portion could be mounted on release ply directly adjacent each other. In such an arrangement, the die cut 36 will be oriented on the ply 12 such that the overlaminate label 38 is comprised in significant part of transparent material. Further, the die cut 28 defining the elongated wristband 30 will include at least part of the portion of the top ply which is not substantially transparent. This will define a print indicia receiving area. The transparent part of the overlaminate label will be sized to cover at least a part of the print indicia receiving area.

If desired, the form 10 may have a pair of release plies in lieu of the single release ply 20 upon which both plies 12 and 40 are mounted. In such a construction a first release ply will be generally coextensive with the transparent ply 12 and a second release ply will be generally coextensive with the paper ply 40. These two parts of the wristband form may then be joined together along adjacent longitudinally extending side edges in any of a number of ways. The two release plies may be overlapped slightly and adhesively joined along their adjacent side edges. Alternatively, the release ply of one part of the form may be overlapped slightly with the top ply of the other part of the form, and the lower surface of the release ply adhesively secured to the top surface of the top ply. As yet a further alternative, the top ply of one part of the form and its associated pressure sensitive adhesive may extend beyond the release ply of that part along a side edge. This exposed adhesive then contacts and engages either the top ply of the other part of the form along the adjacent side edge, or the release ply of the other part of the form along the adjacent side edge. With all of these alternative constructions, top plies of differing materials are provide adjacent each other and secured to generally coextensive release plies.

The wristband form of the present invention finds particular utility in a hospital setting, allowing the hospital staff to keep track of a patient and activities associated with the patient, such as the performance of various diagnostic tests and the administration of various medicines, treatments and therapies. Typically, when an individual is admitted to the hospital as a patient, information will be taken from the patient by a hospital employee in the hospital's admitting department. This information will be entered into the hospital's computerized information processing system. The wristband form 10 of the present invention will be printed at that time with a laser printer, thermal printer, thermal transfer printer, or an ink jet printer in the admitting department. The wristband 30 will typically be printed with the patient's name, as well as additional information, such as for example the name of the patient's physician. The central portion 34 of wristband 30 will also typically be printed with a bar code patient identification number. Because of the opaque, white ink 32 in central portion 34, this printed information will be clearly visible for reading by a hospital employee or for reading by a machine, such as a bar code scanner. At the same time, the labels 50 will be printed with appropriate identifying information, such as the patient's name or the patient's identification number. If desired, the labels 50 may also carry machine readable indicia, such as bar code indicia. Further, labels 54-60 may also be overprinted with appropriate indicia.

Next the wristband 30 is prepared and applied to the patient's wrist. If desired, the form may be separated along perforation line 66 so as to make preparation of the wristband 30 simpler. The overlaminate label 38 is removed from the release ply 20 and applied to the central portion 34 of the wristband 30 so that the indicia printed in portion 34 are covered and protected by the label 38 and, at the same time, clearly visible and readable through the transparent overlaminate label 38. If appropriate, one or more of the labels 54-60 are peeled from the release ply 20 and applied to the wristband 30. The wristband 30 is then peeled from the release ply 20 at the tab portions 62 and 64 and inverted so that the adhesive on the tabs is facing upward. The clasp 70 is then inserted through a hole at one end of the wristband 30. The wristband 30 is wrapped around the patient's wrist and the plastic clasp 70 is inserted through a hole 68 at the opposite end of the wristband 30. The clasp 70 is then snapped shut. The longer of the two tabs, tab 62, is wrapped over and affixed to the outside of the wristband 30.

One or more of the labels 50 on the remainder of the form 10 may be removed from the release ply 20 and applied to the patient's chart for identification purposes. The remainder of the form 10, carrying a plurality of labels 50, can now be attached to the patient's chart for later use. These labels may for example be applied to various reports and forms, as well as medicines and other items associated with the patient.

Having described the invention in detail and by reference to preferred embodiments thereof, it will be apparent that modifications and variations are possible without departing from the scope of the invention defined in the appended claims.

What is claimed is:

1. A patient wristband form, comprising:
a transparent ply having an upper surface and a lower surface,
a pressure sensitive adhesive coating on said lower surface of said transparent ply,
a release ply having an upper surface and a lower surface, said release ply having a release coating on said upper surface of said release ply, said transparent ply being removably mounted on said upper surface of said release ply by said pressure sensitive adhesive coating,
a die cut in said transparent ply defining an elongated wristband,
an opaque coating on said upper surface of said transparent ply in a central portion of said elongated wristband, and
a die cut in said transparent ply defining an overlaminate label, said overlaminate label being separate from said elongated wristband and sized to cover at least a part of said central portion of said elongated wristband so as to cover indicia printed on said opaque coating.

2. The patient wristband form of claim 1, in which said release ply is substantially larger than said transparent ply, and further comprising a paper ply having an upper surface and a lower surface, said lower surface of said paper ply having a pressure sensitive adhesive coating, and wherein said paper ply is mounted on said release ply by said pressure sensitive adhesive.

3. The patient wristband form of claim 2, in which one or more labels are defined by die cuts in said paper ply.

4. The patient wristband of claim 1 in which said transparent ply defines a plurality of colored labels that may be affixed to said elongated wristband.

5. The patient wristband of claim 1 in which said pressure sensitive adhesive coating on said lower surface of said transparent ply is pattern coated such that area beneath said elongated wristband central portion is free of adhesive.

6. The patient wristband of claim 1 in which said transparent ply is die cut to define one or more additional labels.

7. The patient wristband of claim 2 in which said transparent ply and said paper ply are directly adjacent each other so as to provide a patient wristband form of substantially uniform thickness, whereby said form may advantageously be printed by means of a laser printer, thermal transfer printer, or an ink jet printer.

8. The patient wristband of claim 7 in which said release ply defines a perforation line extending there across between said transparent ply and said paper ply.

9. The patient wristband of claim 1 in which said transparent ply further defines one or more circular die cut holes in said elongated wristband adjacent each end thereof, whereby said elongated wristband may be secured in place around the wrist of a patient by a clasp which engages one hole at each end of the wristband.

10. The patient wristband of claim 1 in which said opaque coating on said upper surface of said transparent ply in a central portion of said elongated wristband comprises a coating of a white, opaque ink.

11. The patient wristband of claim 1 in which said transparent ply comprises a ply of film material.

12. The patient wristband of claim 11 in which said transparent ply comprises a ply of substantially clear polyester film material.

13. A patient wristband form, comprising:
a top ply having at least a portion which is substantially transparent and a portion which is not substantially transparent, said top ply having an upper surface and a lower surface,
a pressure sensitive adhesive coating on said lower surface of said top ply,
a release ply having an upper surface and a lower surface, said release ply having a release coating on said upper surface of said release ply, said top ply being removably mounted on said upper surface of said release ply by said pressure sensitive adhesive coating,
a die cut in said top ply defining an elongated wristband, said wristband including at least part of said portion of said top ply which is not substantially transparent, whereby a print indicia receiving area is defined in a central portion of said elongated wristband, and
a die cut in said transparent portion of said top ply defining an overlaminate label, said overlaminate label being separate from said elongated wristband and sized to cover at least a part of said print indicia receiving area.

14. The patient wristband form of claim 13, in which said release ply is substantially larger than said top ply, and further comprising a paper ply having an upper surface and a lower surface, said lower surface of said paper ply having a pressure sensitive adhesive coating, and wherein said paper ply is mounted on said release ply by said pressure sensitive adhesive.

15. The patient wristband form of claim 14, in which one or more labels are defined by die cuts in said paper ply.

16. The patient wristband of claim 13 in which said top ply defines a plurality of colored labels that may be affixed to said elongated wristband.

17. The patient wristband of claim 13 in which said pressure sensitive adhesive coating on said lower surface of said top ply is pattern coated such that area beneath said elongated wristband central portion is free of adhesive.

18. The patient wristband of claim 13 in which said top ply is die cut to define one or more additional labels.

19. The patient wristband of claim 14 in which said top ply and said paper ply are directly adjacent each other so as to provide a patient wristband form of substantially uniform thickness, whereby said form may advantageously be printed by means of a laser printer, a thermal transfer printer, or an ink jet printer.

20. The patient wristband of claim 19 in which said release ply defines a perforation line extending there across between said top ply and said paper ply.

21. The patient wristband of claim 13 in which said top ply further defines one or more circular die cut holes in said elongated wristband adjacent each end thereof, whereby said elongated wristband may be secured in place around the wrist of a patient by a clasp which engages one hole at each end of the wristband.

22. The patient wristband of claim 13 in which said portion of said top ply which is not substantially transparent and which defines said print indicia receiving area includes a coating of a white, opaque ink.

* * * * *